(12) United States Patent
Bargh

(10) Patent No.: US 8,563,301 B2
(45) Date of Patent: Oct. 22, 2013

(54) BIOREACTOR SYSTEMS AND ASSOCIATED METHODS OF PROCESSING BIOREACTOR VESSELS

(75) Inventor: Adrian Neil Bargh, Royston (GB)

(73) Assignee: The Automation Partnership Ltd., Royston, Hertfordshire (GB)

(*) Notice: Subject to any disclaimer, the term of this patent is extended or adjusted under 35 U.S.C. 154(b) by 501 days.

(21) Appl. No.: 12/801,559

(22) Filed: Jun. 15, 2010

(65) Prior Publication Data

US 2011/0003323 A1   Jan. 6, 2011

(30) Foreign Application Priority Data

Jul. 1, 2009   (EP) ..................................... 09164322

(51) Int. Cl.
| *C12M 1/02* | (2006.01) |
| *C12M 3/00* | (2006.01) |
| *B01F 7/00* | (2006.01) |

(52) U.S. Cl.
USPC .................. 435/303.3; 435/288.1; 435/305.1; 435/305.2; 435/288.3; 435/288.4; 435/303.1; 435/289.1; 366/197; 366/292; 366/331

(58) Field of Classification Search
USPC .......... 435/289.1, 303.1, 288.1, 305.1, 305.2, 435/288.3, 288.4, 303.3; 366/197, 292, 331
See application file for complete search history.

(56) References Cited

U.S. PATENT DOCUMENTS

| 6,361,203 | B1* | 3/2002 | Akporiaye ..................... 366/297 |
| 6,962,674 | B2* | 11/2005 | Dean et al. .................... 422/68.1 |
| 2002/0090320 | A1* | 7/2002 | Burow et al. .................. 422/64 |
| 2002/0132286 | A1 | 9/2002 | Downs | |
| 2004/0033588 | A1* | 2/2004 | Su et al. ....................... 435/283.1 |
| 2004/0086956 | A1* | 5/2004 | Bachur, Jr. .................... 435/34 |
| 2004/0157322 | A1* | 8/2004 | Downs et al. ............... 435/295.1 |
| 2005/0277184 | A1* | 12/2005 | Bargh ......................... 435/286.7 |
| 2006/0141614 | A1 | 6/2006 | Puskeiler et al. | |
| 2006/0257998 | A1 | 11/2006 | Klaus et al. | |
| 2009/0137026 | A1 | 5/2009 | Kobayashi et al. | |
| 2012/0218855 | A1* | 8/2012 | Kunas et al. ................ 366/150.1 |

FOREIGN PATENT DOCUMENTS

| CN | 2599006 Y | 1/2004 |
| EP | 1657301 A1 | 5/2006 |
| WO | 0214539 A1 | 2/2002 |
| WO | 2008055652 A2 | 5/2008 |

* cited by examiner

*Primary Examiner* — Nathan Bowers
(74) *Attorney, Agent, or Firm* — Roylance, Abrams, Berdo & Goodman, LLP

(57) ABSTRACT

A bioreactor processing unit (10) includes at least one cell culture module (200) comprising: a base (202) including a receiving station (204) for removably receiving a plurality of bioreactor vessels (400) at respective locations (206); and a clamp plate (240). The clamp plate (240) is removably connectable to the base (202). The system further includes a drive mechanism (226) and multiple fluid conduits. When the system is to be used for an experiment run, vessels (400) are loaded into the receiving station (204) and the clamp plate (240) is connected to the base (202), forming a connection between the drive mechanism and the vessels, for transmitting input motion from the drive mechanism (226) into multiple rotary motion outputs for turning a stirrer (416) in each vessel (400). At the same time, connection of the clamp plate to the base forms a fluid connection between the multiple fluid conduits and an input port (412) in each respective vessel via associated multiple outlet ports (256) in the clamp plate and associated fluid connectors. The system further includes at least one sensor (126*a*, 126*b*) that is mounted so as to be movable to a position adjacent to each respective vessel location (206) for monitoring the contents of each vessel (400).

30 Claims, 6 Drawing Sheets

BIOREACTOR SYSTEMS AND ASSOCIATED METHODS OF PROCESSING BIOREACTOR VESSELS

This application claims priority under 35 U.S.C. §119 to European Patent Application No. 09164322.1 filed on Jul. 1, 2009, the entire disclosure of which is hereby incorporated herein by reference.

FIELD OF THE INVENTION

The invention relates generally to the field of bioreactor processing systems for the suspension cell cultures. More particularly, the invention concerns improvements to cell culture modules within bioreactor systems and to improved methods of processing bioreactor vessels within those systems.

BACKGROUND TO THE INVENTION

Cell cultures, consisting of cells growing suspended in a growth media, or on the surface of suspended particles, in solution are produced within bioreactors with careful control of a number of parameters. These bioreactors may be capable of processing large quantities of cell culture solution. For example, large-scale bioreactors can have capacities from 1-20,000 litres, or even up to 50,000 litres.

Within the bioreactor it is important to carefully control the environment to which the cells are exposed. Subtle changes in the environment can have major effects on the physiology of the cells and the amount of the target product (product titre), for example a recombinant protein, that is produced by each cell. This in turn has a major impact on the economics of the production process. The parameters that must be controlled include the concentrations of oxygen and carbon dioxide available to the cells (dissolved oxygen and $CO_2$), pH, temperature, and specific nutrient levels such as the concentration of glucose. Additionally the physical environment is critical; particularly important components including the form of the gas distribution e.g. bubble size and overall gas flow. Finally, the mixing of the liquid and cells is critical having an impact on the homogeneity within the reactor and hence the local environmental variation to which cells within a bioreactor are exposed. Such issues become significant in very large bioreactors.

The major challenge facing companies manufacturing products in bioreactor systems is the optimisation of the conditions within a bioreactor for the production of a particular product. Optimisation of conditions for a particular cell line producing a particular product can easily have magnitude level effects on the yield of the product, this in turn having a massive impact on the economics of production. Addressing this issue is not simple; there are many parameters to be controlled and the optimal approach may involve variations in these conditions over time. However, it is impractical to explore the impact of varying a range of parameters due to the lack of availability of equipment and the huge costs of operation. The actual costs of one run of a 2l bioreactor can be over $2000. At larger scales the cost rapidly becomes prohibitive. Such issues prevent the application of modern statistical based experiment approaches to resolving the impact of multiple parameter variation typically referred to as DOE (Design of Experiment), such approaches typically requiring tens of bioreactor experiments to have value.

The opportunity for such work to have value has increased over recent years as regulatory authorities have introduced initiatives in which variations within a production run do not necessarily mean the automatic failure of a batch IF the impact of such variations in control parameters has previously been explored. This is impossible without small-scale highly parallel models of bioreactors but essential for manufacturers to remain competitive.

A further issue faced by bioreactors is the difficulty of selecting cell lines early in development that are robust and productive in a stirred bioreactor environment. Clearly, where high tens to hundreds of cell lines need to be screened, existing bioreactor systems are impractical.

A number of small-scale approach bioreactors have been tried, e.g. shaken multiwell plates and flasks, but these lack the ability to faithfully reproduce the conditions found in stirred, gassed systems with closed loop control of culture parameters. To date, small-scale experiment runs are generally carried out in individual bioreactors, of 1 to 10 litre capacity, containing cell cultures in solution. These are processed under careful, monitored control for a period of about two weeks. During that period, the input parameters discussed above may be varied between the individual bioreactors, with the contents of the respective bioreactors being monitored so as to determine which set of parameters achieves optimum, desired results. That set of parameters can then be used in order to scale-up the process to full production scale; the objective being to maximise cell production or cell viability, to improve production efficiency and/or to increase product titre yield.

Control of the culture parameters is required from three perspectives: i) the maintenance of a parameter at a defined set-point, within control limits, for a given time; ii) the controlled, planned variation of that parameter over time; and finally iii) the consistency and reproducibility of that parameter from bioreactor to bioreactor and run to run. Once such control is achieved, parameters can be varied and the impact of the variation on productivity determined.

The cell culture solution within the bioreactor is stirred in order to ensure homogeneity. The rate of stirring can have a major impact on the productivity of the culture through the impact of the physical environment of the cells, for example shear, on the viability and productive life of the cells. Additionally, the stirring rate has a direct effect on mixing and therefore the efficiency of mass transfer of gasses from the input stream of bubbles into the liquid phase where it is available to the cells. The balance between stir rates and their potential negative effects and the benefits of good mixing and gas transfer must be established for a particular culture. At manufacturing scale, energy inputs to the reactor additionally become an important economic consideration.

In many existing small-scale systems, the contents of the bioreactor vessels are not stirred, but are instead agitated by shaking. Whereas this simplifies the system, the vessels not requiring individual stirrers, it does not produce accurate simulation of production scale conditions, in which the contents are stirred; shaking does not replicate the shear forces induced in the vessel contents by stirring. Additionally, gas transfer in shaken vessels is primarily through surface aeration rather than bubbles fed into the base of the system, altering the dynamics of the gas transfer and the physical environment.

Where stirrers are provided, each is independently driven from a drive source. It is time-consuming for the operator to connect and disconnect each stirrer to the associated drive source, as is required between experiment runs There are two key aspects to the gas control within bioreactors: that of $CO_2$ and that of $O_2$.

The dissolved oxygen level in the bioreactor must be maintained at a set level to ensure a consistent availability to the cells such that metabolism is not limited. Typical maintenance levels vary between 15 and 50% of the maximum dissolved oxygen level achieved by air saturation. Approaches to achievement of this vary between users, some preferring to use lower input concentrations and higher flow rates, others higher input concentrations and lower flow rates. Control of the input flow rate is critical as it affects the stripping of other gases such as $CO_2$ from the culture media.

The concentration of $CO_2$ that the cells are exposed to can have significant effects on metabolism. Control of $CO_2$ is additionally used to control pH in combination with bicarbonate based buffer systems in the media. Bubbles are also a key source of damage to cells and hence control of the total gas inflow rate is an important factor in maintaining cell viability.

The pH level within the bioreactor should remain within predetermined bounds, which can vary as the cell culture develops. Generally this is achieved by a combination of a bicarbonate based buffer system within the liquid media, combined with the maintenance of a specific level of dissolved $CO_2$. However, above a certain cell density the production of lactic acid by the cells can overwhelm the buffering capability of the media and the pH is maintained within the desired limits by the addition of doses of alkali solutions to combat the increasing acidity. The addition of alkali in bioreactors is controlled as part of a feedback loop including a pH sensor.

Temperature is an important parameter within bioreactors. The temperature used within bioreactors culturing mammalian cells does not vary widely due to the origins of the cells in animals exhibiting control of body temperature. However, some minor variations are used during the period of culture, to effect shifts in metabolism biasing the cell physiology towards production of the recombinant protein rather than cell multiplication for example.

Generally, a heater is controlled in order to increase or decrease the amount of supplied heat. In some systems the culture growth and energy inputs into stirring generate excess heat, so cooling and heat dissipation systems are required.

A range of nutrient feeds may be dispensed into the reactor. Typically these include media feeds which supply additional amino acids and carbon sources to replace those used in cell growth. Multiple different feeds may be added to a bioreactor on different schedules, often including pure carbon sources such as glucose. Generally, such feeds are added in response to the measurement of parameter levels within the bioreactor.

Monitoring of various parameters within the bioreactor is key to their control. Some parameters are controlled through closed loop sensing and response systems, others through sampling and off-line analysis due to the lack of appropriate on-line monitoring systems.

On-line monitoring systems are of two types: invasive and non-invasive. Invasive sensors rely on a probe carrying a sensor being inserted into the vessel and having direct contact with the culture solution. Generally, such systems are reusable and must be cleaned and calibrated between uses. Such monitors contribute to the complexity of setting up bioreactors through the requirement for disassembly from the reactor vessel for cleaning and sterilisation and the requirement for aseptic assembly. Some probes can be sterilised with the vessel but do require removal of residues and cleaning. Non-invasive sensor systems are now available in which a non-disposable sensing component has no contact with the culture, therefore does not require cleaning, sterilisation and accompanying validation of those processes.

One on-line monitoring method is to include disposable sensor spots in the vessel for remote interrogation. For example, a pH and/or dissolved oxygen sensor patches attached to the inside of the vessel can be interrogated externally; the spot is illuminated by a light source and a light detector detects emitted fluorescence, the characteristics and dynamics of which are indicative of the pH or dissolved oxygen levels within the vessel. Other techniques are available, including measurement of light diffraction and reflectance of near-infrared light. In this context, light is defined as encompassing any emission within the electromagnetic spectrum, not just visible wavelengths.

In current small-scale systems where sensing is done by non-invasive interrogation, individual vessels each have respective associated sensing apparatus, such as a light source and associated detector at each vessel location. This is expensive and also problematic in that the individual sensors must each be calibrated to ensure that the monitoring of each vessel is consistent.

The monitoring of the vessel contents may be achieved by invasive methods in which a small sample portion of the cell culture solution is removed for on-line or off-line analysis, for example via sampling port or by aspirating a sample of the solution with a pipette for dispensing for example into the sample cup of an analytical system. Likewise, a sample portion of the gases in the headspace within the vessel may be extracted for analysis in, for example, a gas analyser. That extraction may be done by a probe inserted into the headspace, or via a gas outlet port and associated conduit.

Where the liquid samples and/or the headspace gases are analysed via extraction through an outlet port in each vessel, it is time-consuming and often manually complex for an operator to connect and disconnect the fluid conduits to the respective outlet ports, a primary risk being the contamination of the device to be inserted. Such problems add to the general complexity and cost of conducting multiple bioreactor experiments.

In summary, there is a range of challenges in the development and optimisation of bioreactor based manufacturing processes, including: i) general costs of operation of current systems, even that of small scale systems being prohibitive due to complexity of set-up, labour, capital cost, equipment availability within facilities infrastructure required (steam generation) and high costs of media components per unit volume; ii) lack of directly applicable small-scale systems to model larger bioreactors; and iii) a lack of trained personnel driving the requirement for improved throughput per trained employee.

Accordingly, it is an object of the invention to improve the efficiency of the turnaround between experiment runs in microscale bioreactor systems, reduce labour requirement and increase throughput in laboratories.

It is another object of the invention to provide a more cost-effective solution to the monitoring of multiple individual vessels in a microscale bioreactor system.

SUMMARY OF THE INVENTION

According to a first aspect of the invention, there is provided a bioreactor system, including a cell culture module comprising:
  a. a base including a receiving station for removably receiving a plurality of bioreactor vessels at respective locations;
  b. a drive mechanism; and
  c. a clamp plate, removably connectable to the base and connectable to the drive mechanism, for transmitting input motion from the drive mechanism into multiple rotary motion outputs, each output corresponding to a respective vessel location in the receiving station.

The removable clamp plate facilitates the set up of the system and improves the efficiency of the turnaround between experiment runs because all that is required is to insert the vessels in position within the receiving station, then to connect the clamp plate to the base and the drive mechanism, which action connects the drive mechanism to all of the vessels. There is therefore no need to make individual connections for every vessel.

In one embodiment, the drive mechanism is adapted to convert a single input motion into the multiple rotary output motions. The drive mechanism may be an eccentric drive mechanism that includes an array of fixed drive elements, with the clamp plate including a complementary array of rotatable members, each having an off-axis driven element. The driven element may comprise a pin or hole, with the drive element comprising a respective complementary hole or pin, drive motion being conveyed via a mechanical connection between the respective pins and holes.

The driven element may, in an alternative embodiment, comprise a magnet or a ferromagnetic element, with the drive element comprising a respective complementary ferromagnetic element or magnet, drive motion being conveyed via ferromagnetic forces between the respective magnet and ferromagnetic element.

With such a configuration, all of the vessels can be driven from a single input motion (i.e. a single motor). This clearly cuts down on constructional costs and complexity as compared to a configuration where each vessel has its own drive motor, as in prior art arrangements.

In one embodiment, the drive mechanism is integrally connected with the clamp plate.

Instead of being located, for example, in the base of the cell culture station, by connecting the drive mechanism integrally with the clamp plate there is no need to make a new connection between the clamp plate and the drive mechanism each time the system is set up. Removal of the clamp plate and the drive mechanism is achieved in a single step.

In one embodiment, the system further comprises at least one bioreactor vessel having a stirrer, wherein the at least one vessel is received in the receiving station and wherein a drive connection is established between a respective one of the multiple rotary motion outputs and the stirrer.

In one embodiment, the system further comprises multiple fluid conduits, the clamp plate further comprising fluid connectors for forming a fluid connection between the fluid conduits and associated outlet ports in the clamp plate, each outlet port corresponding to a respective vessel location in the receiving station.

In this embodiment, not only are all of the vessels connected to the drive mechanism by the simple action of connecting the clamp plate to the base, but that same action also forms fluid connections to each of the vessels. In contrast, in prior arrangements the fluid connections to each vessel had to be made individually.

According to a second aspect of the invention, there is provided a bioreactor system, including a cell culture module comprising:
 a. a base including a receiving station for removably receiving a plurality of bioreactor vessels at respective locations;
 b. at least one bioreactor vessel having a stirrer, wherein the at least one vessel is received in the receiving station; and
 c. a drive mechanism comprising at least a portion that is removably connectable to the base for transmitting input motion into multiple rotary motion outputs, each output corresponding to a respective vessel location in the receiving station, wherein a drive connection is established between a respective one of the multiple rotary motion outputs and the stirrer.

Instead of the removable clamp plate, here the removable portion of the drive mechanism facilitates the set up of the system and improves the efficiency of the turnaround between experiment runs because all that is required is to insert the vessel(s) in position within the receiving station, then to connect the removable portion of the drive mechanism to the base (possibly via the remainder of the drive mechanism connected to the base), which action establishes a drive connection to the stirrer of each vessel thereby enabling the transmission of the input of the drive mechanism to multiple rotary motion outputs at the respective vessels. There is therefore no need to make individual connections for every vessel.

In one embodiment, the system may further comprise: multiple fluid conduits; and a clamp plate, removably connectable to the base, and including fluid connectors for forming a fluid connection between the fluid conduits and associated multiple outlet ports in the clamp plate, each outlet port corresponding to a respective vessel location in the receiving station.

According to a third aspect of the invention, there is provided a bioreactor system, including a cell culture module comprising:
 a. a base including a receiving station for removably receiving a plurality of reactor vessels at respective locations; and
 b. multiple fluid conduits; and
 c. a clamp plate, removably connectable to the base, and including fluid connectors for forming a fluid connection between the fluid conduits and associated multiple outlet ports in the clamp plate, each outlet port corresponding to a respective vessel location in the receiving station.

The removable clamp plate facilitates the set up of the system and improves the efficiency of the turnaround between experiment runs because all that is required is to insert the vessels in position within the receiving station, then to connect the clamp plate to the base, which single action connects the multiple fluid conduits in the cell culture station to the respective vessels. There is therefore no need to make individual connections for every vessel.

Where the system according to the first aspect comprises multiple fluid conduits or where the system is in accordance with the second aspect, in one embodiment the system further comprises a valve assembly having multiple fluid supplies, the valve assembly operable to supply a selected fluid to a selected fluid conduit.

In this manner, the fluid connection to each vessel is capable of delivering a selected one (or a mixture of) the fluid supplies to the vessel.

Where the system comprises multiple fluid conduits, in one embodiment the system further comprises at least one bioreactor vessel having a fluid port, wherein the at least one vessel is received in the receiving station and wherein a fluid connection is established between the fluid port in the vessel and a respective one of the multiple outlet ports in the clamp plate.

The system may include a plurality of reactor vessels. In one embodiment, the plurality of vessels are formed as a cassette.

By forming the vessels as a cassette, the vessels can all be inserted or removed from the vessel receiving station as a unit. This would reduce vessel handling time.

In one embodiment, the system further comprises at least one sensor for determining characteristics of the contents of a vessel. The at least one sensor may be mounted so as to be movable to a position adjacent to different respective vessel locations.

According to a fourth aspect of the invention, there is provided a bioreactor system, including a cell culture module comprising:

a. a base including a receiving station for removably receiving a plurality of bioreactor vessels at respective locations; and b. at least one sensor for determining characteristics of the contents of a vessel, the at least one sensor being mounted so as to be movable to a position adjacent to different respective vessel locations.

By having the at least one sensor mounted so as to be movable to a position adjacent to different respective vessel locations, that sensor is able to interrogate and monitor each of those vessels. Thus, all of the vessels could be monitored by using just a single sensor. This is in contrast to prior arrangements, where each vessel had its own monitoring sensor or sensors. Since the sensors add to the cost of the system, reducing the number of sensors reduces the cost and complexity of the system, albeit that the cost savings are partially offset by the cost of the positioning system. In addition, by using a single sensor, it is assured that the readings taken at the different vessel locations will be consistent; there is no need to calibrate each of an array of sensors to ensure consistency of readings.

In one embodiment, the at least one sensor is for detecting one of: the DO concentration, the $CO_2$ concentration, the pH, the temperature, cell count, cell viability, cell size, biomass, metabolites, other biological molecules and particle distribution.

The at least one sensor may comprise a light source and a light detector, to determine the characteristics through interrogation of a sensor spot on a vessel.

The at least one sensor may be mounted on an X-Y positioning device.

In one embodiment, the system further comprises a bed station, on which the cell culture module is mounted or on which multiple cell culture modules are mounted.

In one embodiment, the system further comprises a liquid handling station, comprising a liquid handling robot that is capable of addressing each vessel location and dispensing and/or aspirating fluids to and from vessels at those locations.

In one embodiment, where the system includes at least one bioreactor vessel, the liquid handling robot is capable of opening a fluid port in that vessel.

According to a fifth aspect of the invention, there is disclosed a method of processing bioreactor vessels, comprising the steps of:

a. placing the system as described above in a controlled environment;

b. removing a vessel from aseptic packaging within that controlled environment; and c. inserting the vessel into the receiving station.

The controlled environment may comprise a laminar flow cabinet.

Where the system includes a clamp plate, the method may further comprise the step of sterilising the clamp plate between uses.

BRIEF DESCRIPTION OF THE DRAWINGS

The invention will be described, by way of example, with reference to the accompanying drawings, in which.

DETAILED DESCRIPTION

Figure 1:
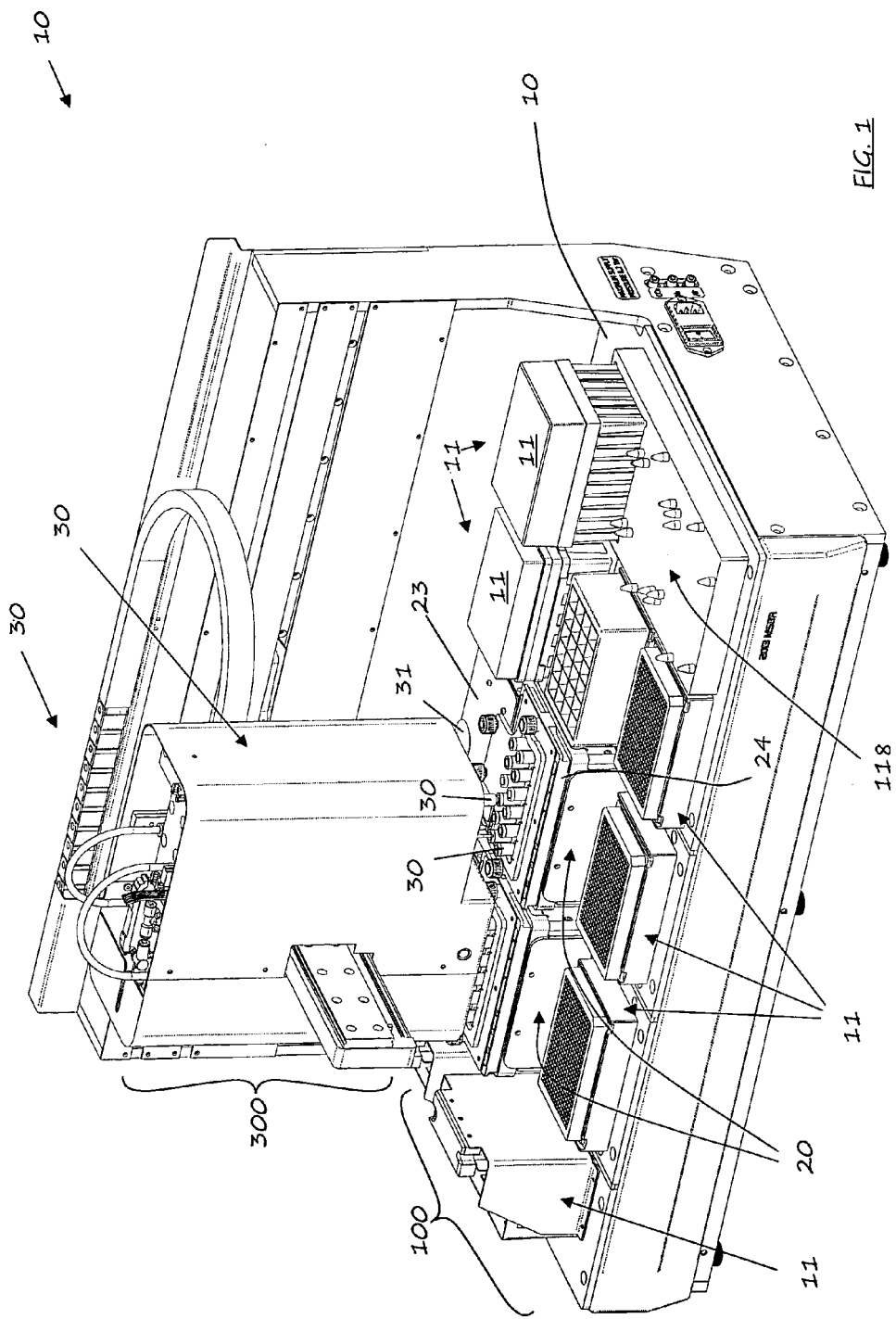
FIG. 1 is a perspective overview of an automated microscale bioreactor system according to an embodiment of the invention.

A bioreactor processing system 10 comprises, generally, a bed station 100 and a liquid handling station 300, which may be interconnected (as shown in FIG. 1) or may be separate from one another.

The bed station 100 comprises a frame 102 on which are mounted various modules. The modules include at least one cell culture module 200, which is described in greater detail below with reference to FIGS. 3a and 3b, and, optionally, one or more well plate modules 112, pipette tip box modules 114, pipette tip waste modules 116 and lid storage modules 118. Each module may include a removable lid 111. A well plate module 112 may contain one or more wells, which may be shallow or deep. Accordingly, each of a microtitre or multiwell plate and a rack of tubes is intended to fall within the definition of well plate module.

The liquid handling station 300 includes a head 302 mounted on a conventional X-Y positioning robot 304. The head 302 includes components that are selectively moveable along the Z axis. The head 302 is thus being capable of addressing and interacting with each of the modules, as will be described in greater detail below.

Bioreactor Vessels

Figure 2:
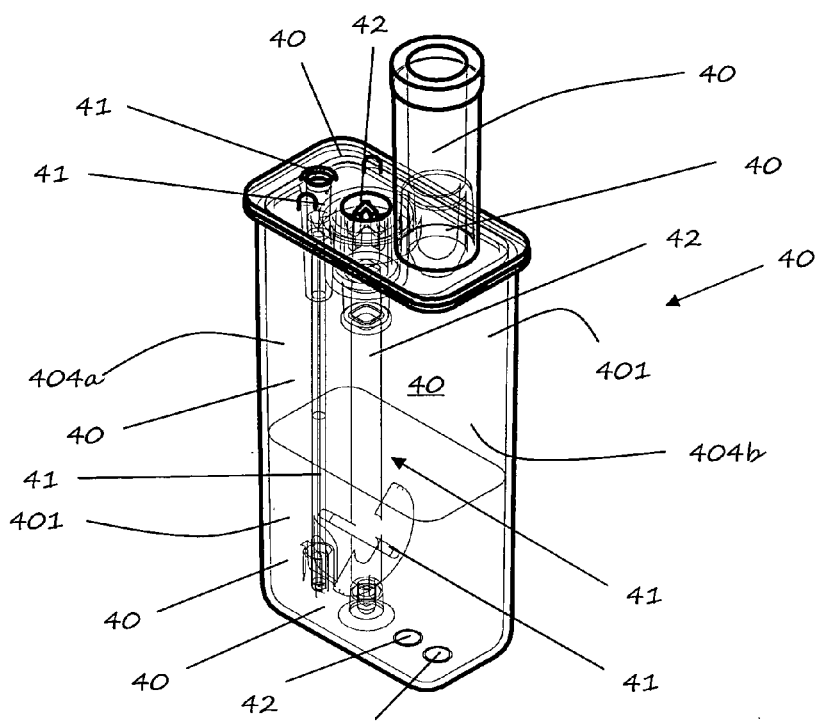
FIG. 2 is a perspective view of a bioreactor vessel for use in the system of the invention.

With reference to FIG. 2, a microscale bioreactor vessel 400 for use with the inventive bioreactor system 10 comprises front, back, top, bottom and side walls 401a, 401b, 402, 403, 404a, 404b defining a chamber 405 for receiving a cell culture solution 407 having a headspace 409 above. The top wall 402 includes a fluid transfer port 406, on which is removably attached a cap 408. The vessel further includes a sparge tube 410, having a gas input port 412 in the top wall 402 of the vessel. The gas input port 412 includes a filter 414.

A stirrer 416 comprising blades 418 mounted at the base of a vertical shaft 420 is rotatably mounted within the vessel 400. The upper end of the shaft 420 includes a drive input 424.

A pH sensor spot 426 and a DO sensor spot 428 are disposed on the bottom wall 403, such that they are able to detect the pH and DO levels of the solution 407 and to be interrogated from the exterior of the vessel 400.

Venting of the vessel chamber 405 is achieved via a labyrinthine path connecting the headspace 409 to atmosphere via the stirrer shaft drive input 424. Alternatively, a separate vent port may be provided towards the top of the vessel 400.

Cell Culture Modules

Figure 3A:
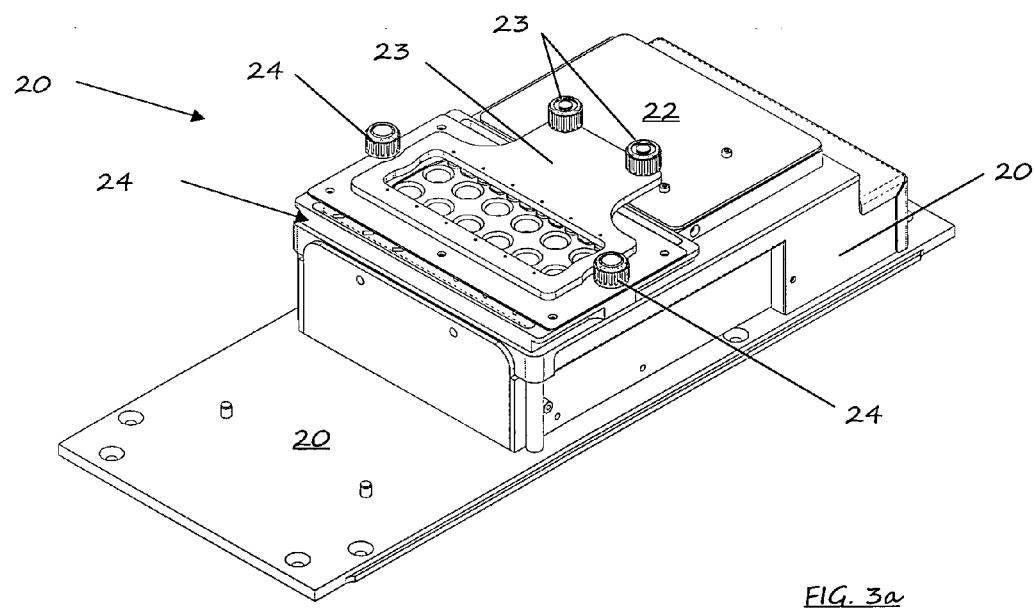
FIG. 3a is a perspective view of a cell culture module, which comprises part of the system of the invention.
Figure 3B:
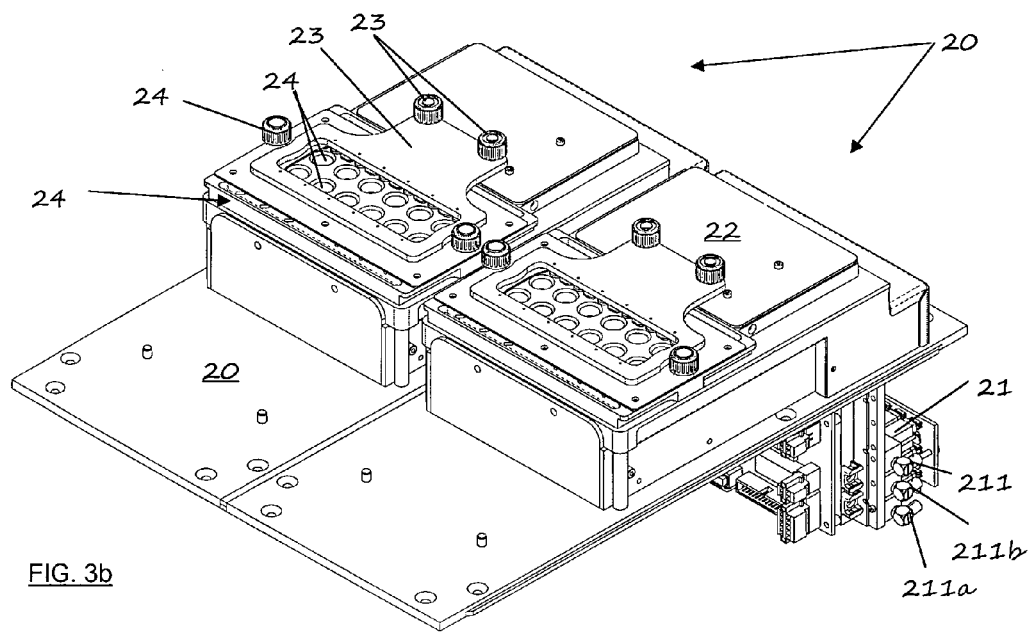
FIG. 3b is a perspective view of a pair of cell culture modules, side-by-side.
Figure 5:
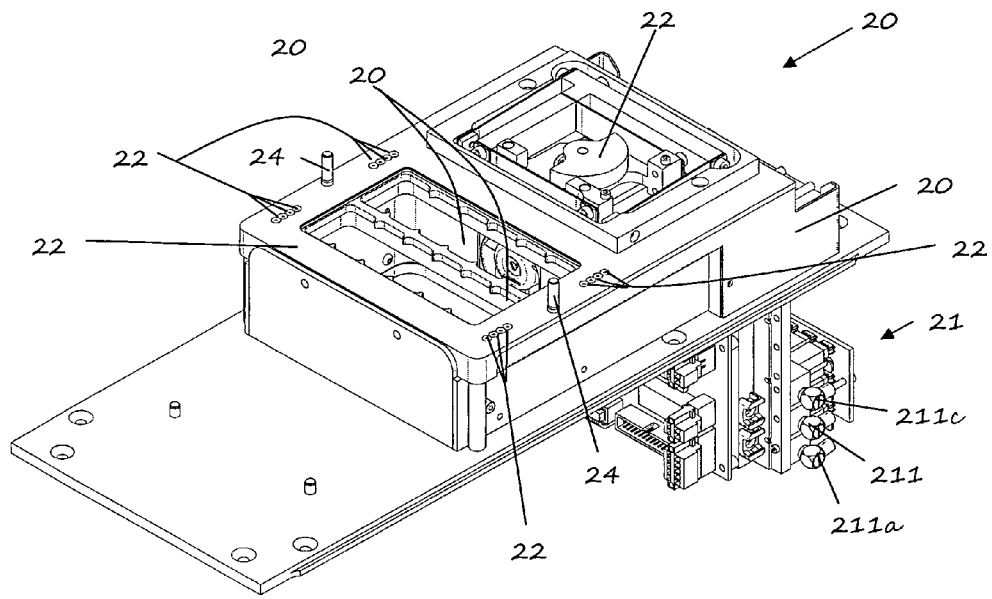
FIG. 5 is a perspective view of a cell culture module, with drive coupling and clamp plate removed.

As shown in FIG. 1, the bioreactor processing system 10 comprises a pair of cell culture modules 200 mounted to the deck 102 of the base station 100. That pair of cell culture modules 200 is shown in isolation in FIG. 3b. It will be understood, however, that the system may include just a single such cell culture module 200 or more than two such cell culture modules 200. For the purposes of description, reference is made to FIG. 3a, showing a single cell culture station 200 in isolation, and also to FIG. 5, which corresponds, but has some parts removed for clarity.

The cell culture module 200 comprises a base 202 mounted on a base plate 201. The base plate 201 is removably connectable to the base station 100. The cell culture module base 202 includes a receiving station 204 for removably receiving a plurality of bioreactor vessels 400. In the illustrated embodiments, the receiving station 204 can hold up to twelve vessels 400 in two rows of six at respective locations 206. Thus, the bioreactor processing system 10 having a pair of such modules 200 has the capacity to process up to 24 vessels simultaneously. It will be appreciated, however, that the receiving station 204 could be designed to accommodate a greater or lesser number of vessels 400 and that the vessels 400 could be arranged in any suitable configuration.

One or more heaters (not shown) are located adjacent to the vessel receiving locations 206 to control the temperature of the vessels.

A valve assembly 210 is mounted to the underside of the cell culture module base 202. The valve assembly 210 is received in a cavity of the bed station 100 when the cell culture module 200 is connected to the bed station.

Figure 8:
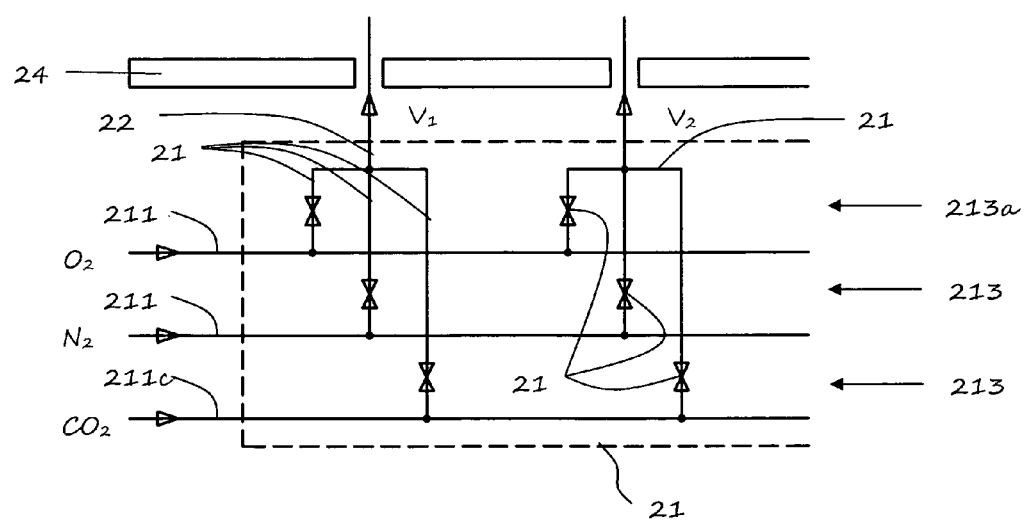
FIG. 8 is a schematic view of gas supplies and associated valve assembly.

With reference also to FIG. 8, the valve assembly 210 has three input ports 211a-c, respectively connectable to $O_2$, $N_2$ and $CO_2$ gas supplies. A bank of valves 213a-c is associated with each respective input port 211a-c, each bank 213a-c comprising a valve 214 for each vessel receiving location 206. Thus, in the illustrated embodiment, the valve assembly comprises a total of 36 valves 214. From another point of view, each vessel receiving location 206 has three associated valves 214: one to control the supply of $O_2$, another to control the supply of $N_2$ and another to control the supply of $CO_2$.

Each valve 214 has an outlet port 216 to which is connected an output conduit 218. The valves 214 are grouped according to the vessel receiving location 206 to which they correspond, and the output conduits 218 for each group are joined to a proximal end of a respective transport conduit 220. There is therefore a transport conduit 220 associated with each vessel receiving location 206. The distal end of each transport conduit 220 is connected to a respective outlet port 222 on an upper surface 224 of the base 202.

The cell culture module base 202 further includes a drive mechanism, indicated generally at 226. The drive mechanism includes a motor (not shown) connected to a parallelogram linkage 228 to produce an eccentric output motion. A drive coupling 230 is connected, via thumbscrews 232, to the parallelogram linkage and is hence driven in an eccentric manner.

Figure 4:
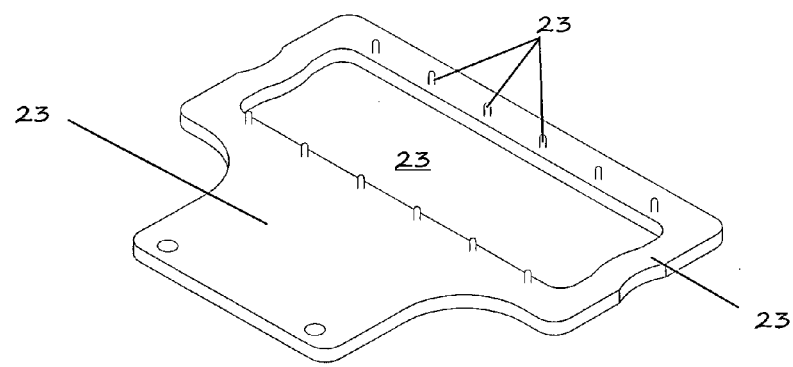
FIG. 4 is a perspective view of a drive coupling, showing projecting drive pins.

As best seen in FIG. 4, the drive coupling 230 is a plate-like structure, having an array of twelve drive pins 234 projecting from the underside 236 thereof, each pin 234 corresponding to one of the vessel receiving locations 206. The drive pins 234 are arranged in two rows of six on either side of a cut-out 238 that extends through the centre of the structure for a purpose to be explained below.

A clamp plate 240 is removably connected to the cell culture module base 202, in a position overlying the vessel receiving station 204, by a pair of nuts 242 received on corresponding threaded posts 244 projecting from the upper surface 224 of the base. The nuts 242 preferably include a knurled exterior surface so as to be turnable without the use of tools. The clamp plate 240 is a generally rectangular, planar member having an array of relatively large circular apertures 246 arranged in two rows of six, in positions corresponding to the vessel receiving locations 206.

Figure 6A:
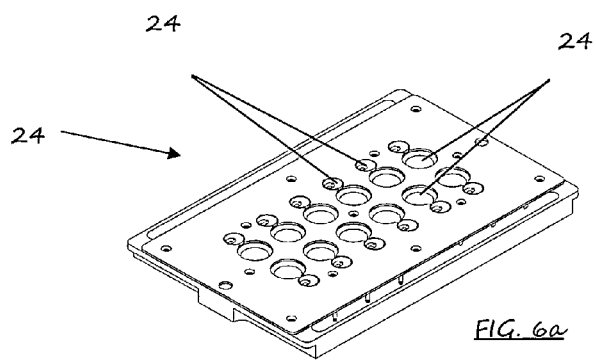
FIGS. 6a and 6c are, respectively, top perspective and partial views of a clamp plate.

See FIG. 6a. As described below, these apertures 246 are to accommodate the upstanding fluid transfer ports 406, with or without the associated caps 408 attached, of respective vessels 400 when received in the respective vessel receiving locations 206.

Adjacent to each of the relatively large apertures 246 is a smaller circular hole 248. A shaft 250 is rotatably received in each of these smaller holes 248, each shaft having an off-axis hole 252 sized and positioned to receive a respective one of the drive pins 234 of the drive coupling 230. See FIG. 6c. The apertures 246 and the holes 248 all extend from top to bottom through the clamp plate 240. The underside of each shaft 250 has a drive element 254 for forming a drive connection with the drive input 424 of the stirrer 416 of a respective vessel 400.

Figure 6B:
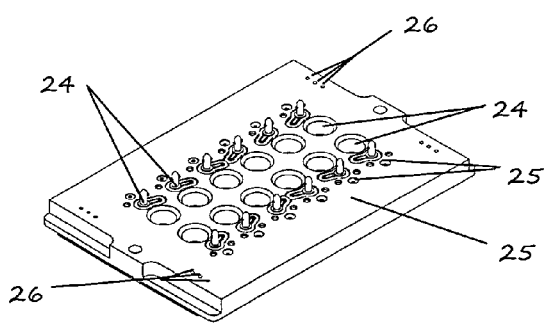
FIG. 6b is a bottom perspective view of the clamp plate.
Figure 6C:
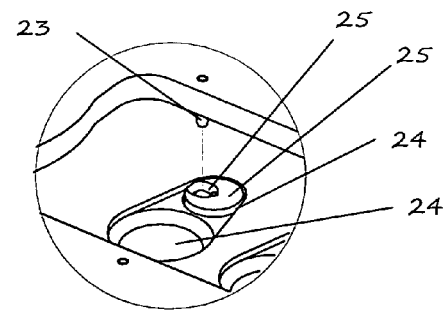
Figure 7:
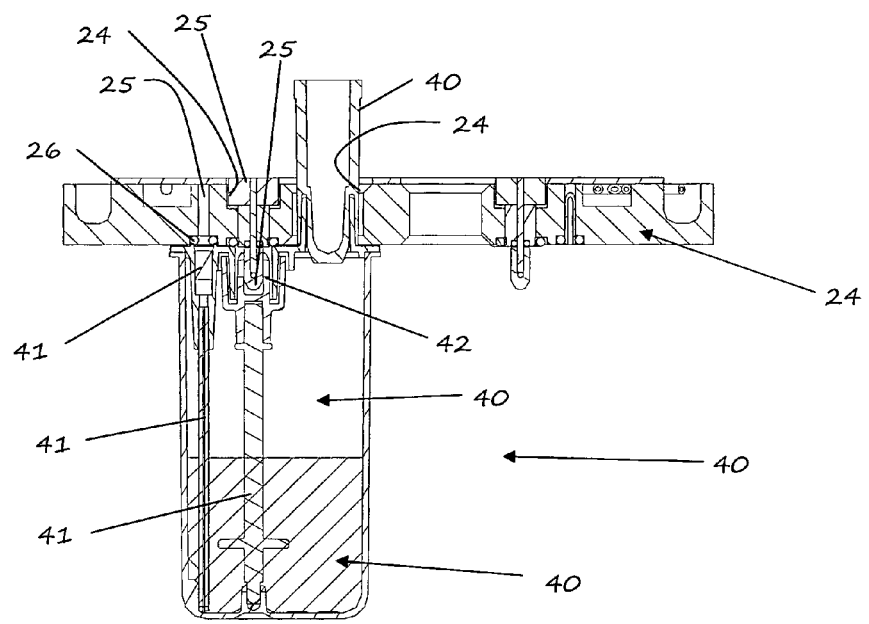
FIG. 7 is a schematic cross-sectional view of the interface between the clamp plate and the upper end of a vessel.

Twelve gas outlet ports 256 are located, in two rows of six, on the underside 258 of the clamp plate 240 adjacent to the holes 248, as shown most clearly in FIG. 6b. The outlet ports 256 are aligned with the gas input ports 412 of the respective vessels 400. Sealed connections are formed between the respective outlet ports 256 and input ports 412 by virtue of an associated o-ring [ref] surrounding the outlet port 256. Twelve gas inlet ports 260 are located, in groups of three, at the corners of the underside 258 of the clamp plate 240. These inlet ports 260 are aligned with and form a sealed connection with the corresponding outlet ports 222 on the upper surface 224 of the base 202 when the clamp plate 240 is secured to the base 202.

Each clamp plate outlet port 256 is fluidically connected to a respective one of the clamp plate inlet ports 260. The fluid connection may be made by means of plugged cross-drillings within the clamp plate 240. Alternatively, the fluid connection may be made via a flexible tube having a proximal end sealingly connected to a fluid terminal of the input port 260 and a distal end sealingly connected to a fluid terminal of the output port 256.

In this manner, each vessel 400 is connected to each of the gas supplies via the following path: gas supply; valve assembly 210 via input port 211a-c; through selectively opened valve 214; via output conduit 218 to transport conduit 220; to cell culture module base outlet port 222; to clamp plate inlet port 260; via fluid connection to clamp plate outlet port 256; to input port 412 in vessel.

Sensor Arrangement

Figure 9:
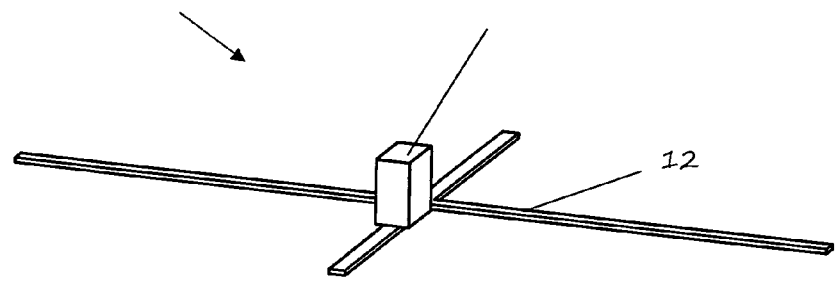
FIG. 9 is a schematic view of a sensor head mounted on an X-Y positioning apparatus.

A sensor assembly 120, shown schematically at FIG. 9, is housed within the cavity defined by the frame 102 of the bed station 100. A sensor head 122 is mounted on an X-Y positioning device 124 for two-dimensional horizontal positioning within the cavity. The sensor head 122 is thus able to be moved to and between respective sensing locations beneath the cell culture modules 200. Each sensor spot 426, 428 of each vessel 400 has an associated sensing location.

The sensing location will depend upon the type of sensor that is used. In the illustrated embodiment, in which each vessel 400 has both a pH sensor spot 426 and a DO sensor spot 428 on the bottom wall 403, the sensing locations for those spots are beneath the bottom wall 403. If the sensor spots were located on a side wall 404a, 404b, for example, the sensing locations might instead be adjacent to that side wall.

Figure 10:
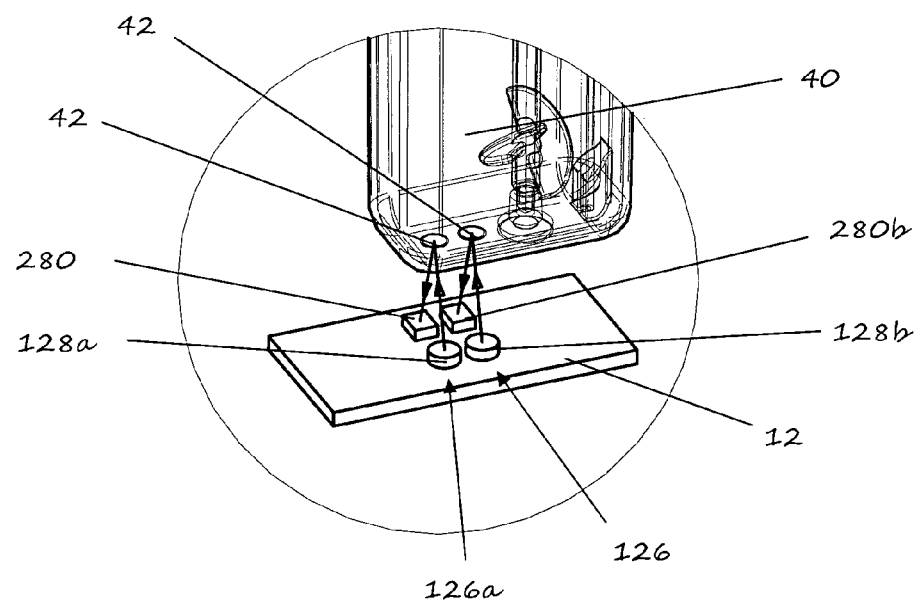
FIG. 10 is a detail schematic view of the sensor head, showing the interrogation of sensor spots on the underside of a vessel.

As shown in FIG. 10, the sensing head 122 includes two sensors 126a, 126b, for respectively interrogating the pH sensor spot 426 and the DO sensor spot 428. Each sensor comprises a light source 128a, 128b and a light detector 280a, 280b. Light emitted from the light source 128a, 128b is incident on the associated spot 426, 428 when the sensing head 122 is in the sensing location for that particular spot. The properties of the incident light are altered by the spots 426, 428, dependent on the characteristics of the cell culture solution 407, as will be understood by the person skilled in the art. The detectors 280a, 280b detect the light reflected from the associated spots 426, 428; changes in the properties of the reflected light, such as fluorescence or diffraction, compared to the emitted light being detected to provide a reading indicative of the characteristics of the cell culture solution 407 within the vessel. Such a spot/detector combination is known in the art as an optical chemical sensor.

By having a single sensing head 122, movable to a position adjacent to each spot 426, 428 at each respective vessel location, the cost of the sensor arrangement 120 is greatly reduced in comparison with prior art sensor arrangements where a sensor is provided for each respective spot at each vessel location. Of course, having a single sensing head 122 means that it takes longer to interrogate an array of vessels 400 than if each vessel had its own sensor arrangement. To mitigate for this, and yet to provide a balance between cost and speed of interrogation, an array of sensing heads may be provided. For example, two sensing heads 122, if suitably arranged and mounted could be moved together to halve the interrogation time for the array. The heads 122 could be arranged side-by-side in order to interrogate adjacent vessels 400 simultaneously. Alternatively or additionally, the sensing heads 122 could be arranged at corresponding positions beneath adjacent cell culture modules 200, so that each module can be interrogated at the same time. Naturally, any suitable combination and configuration could be employed, with apparatus costs and speed of interrogation increasing with increased sensors.

Liquid Handling Station

With reference again to FIG. 1, the head 302 of the liquid handling station 300 includes a pipette tip handler that is selectively movable along the Z-axis and adapted to pick a pipette tip 306 and to dispense and/or aspirate fluids through the pipette tip. The head 302 also includes a capping device 308, also selectively movable along the Z-axis, for removing and replacing the vessel fluid transfer port caps 408. The head 302 further includes a suction cup 310 selectively movable along the Z-axis for removing and replacing the module lids 111.

Use of the Bioreactor Processing System

In order to carry out an experiment run, the or each cell culture station base 202 is loaded up with vessels 400, each vessel being placed in a respective vessel receiving location 206 within the receiving station 204. The vessels 400 may be provided in aseptic packaging. To minimise the risk of contamination, the insertion of the vessels 400 into the receiving station 204 may take place within a controlled environment. The controlled environment may, for example, be a biological safety cabinet, such as a laminar flow cabinet, which may be fitted with, for example, a HEPA filter to prevent biological material contaminating the cell culture.

The clamp plate 240 is then placed on top of the base 202 and secured in position by screwing the nuts 242 onto the threaded posts 244 on the upper surface 224 of the base 202. The vessel fluid transfer ports 406 and attached caps 408 project through the respective larger apertures 246 in the clamp plate 240. In addition, the clamp plate inlet ports 260 are aligned with and form a sealed connection with the corresponding outlet ports 222 on the upper surface 224 of the base 202. An additional sealing member, such as an o-ring 262, may reinforce the seal.

Next, the drive coupling 230 is attached in place by screwing the thumbscrews 232 to the parallelogram linkage 228 of the drive mechanism 226. The vessel fluid transfer ports 406 and caps 408 project through cut-out in the drive coupling 230. The drive pins 234 of the drive coupling 230 are received in the respective off-axis holes 252 in the shafts 250. When, during the experiment run, the drive mechanism 226 is actuated, it drives the drive coupling 230 in an eccentric motion 228. That eccentric input motion is converted, via the drive pins 234 received in the off-axis holes 252, into rotary motion of each of the shafts 250 within the holes 248. Those multiple rotary outputs rotate the respective stirrers 416 via the drive connection between the drive element 254 and the drive input 424 of the stirrer 416.

The vessels 400 may be supplied pre-loaded with cell culture solution 407. Alternatively, the vessels 400 may be supplied empty, the cell culture solution 407 being inserted via the respective fluid transfer ports 406 once the vessels are received in their respective locations 206. That insertion may be carried out manually, or automatically by means of the liquid handling station 300.

The liquid handling station head 302 is adapted to dispense liquids (such as nutrients, base to control acidity, etc.) into the vessels 400, via a pipette tip 306. In order to access the fluid transfer port 406, the cap 408 must first be removed. This is achieved by the capping device 308, which is able to grip and remove the cap 408 and then to replace the cap after the liquid handling operation.

The pipette tips 306 are disposable, to avoid contamination and/or cross-contamination between the vessels 400. The pipette tip handler is adapted to pick a sterile pipette tip 306 from a tip box module 114 and, after is has been used for a liquid handling operation, to jettison the tip 306 to waste within a tip waste module 116. The pipette tip box may optionally be supplied with a lid which the liquid handler may remove with the suction cup 310.

Another function of the liquid handling station head 302 is to aspirate samples from the vessels 400 via pipette tips 306 inserted into the respective fluid transfer ports 406 (having temporarily removed the associated caps 408) and subsequently to dispense the aspirated samples into individual wells within a multi-well plate or into a rack of tubes at a well plate module 112. The individual samples of cell culture solution 407 can then be analysed in an off-line analysis device to detect, for example, one or more of: cell count; cell viability; cell size; biomass, metabolites and biological molecules.

A sample cup (not shown) can be fitted to the system and connected to a cell counter or a biomass or metabolite analyser. The liquid handling station 300 may be adapted to dispense samples into the sample cup for on-line analysis of the samples.

As described above, each module may include a lid 111. Accordingly, where a lid is in place on a module, a preliminary handling operation of removing the lid is required. This is achieved by means of the suction cup 310 on the liquid handling station head 302, which is able to grip the lid 111 and to hold it until the operation involving that module has ended, when the suction cup 310 can release the grip to replace the lid. Rather than hold the lid 111 throughout the operation, the head 302 may be operated to place the lid 111 temporarily on a lid storage module 118, later to be collected and replaced on the appropriate module.

Monitoring and Control

As an experiment run progresses, the cell culture solution 407 in each vessel 400 develops and has different requirements for optimum growth and production of target proteins and/or antibodies. Accordingly, the input parameters do not remain fixed throughout the experiment run but instead follow a profile. For example, in early stages of development, the cell culture may require a slightly more alkali environment as compared to later developmental stages.

During an experiment run, each vessel is individually monitored for pH and DO via the interrogation of the respective sensor spots 426, 428 by the sensor assembly 120.

The data stream from the sensor assembly 120 can be used as input to a control system for feedback control of the input parameters for the individual vessels 400. For example, the data from the pH sensor 126a can be used as an input to determine the quantity of $CO_2$ supplied to the individual vessels 400 with a view to keeping the pH within a predetermined profile.

The temperature of each culture station module 200 is also monitored by an associated temperature sensor. The data from the temperature sensors can be used as input to the heater(s) to ensure that the vessels 400 in the corresponding culture station module are maintained at a predetermined temperature profile.

As mentioned in the introductory portion of this description, the objective of an experiment run is to determine which set of input parameters provides optimum results. Accordingly, each vessel 400 in the unit 10 may be run with a slightly different set of parameters than the others. For example, different vessels 400 may be run with one or more of the following varied as compared to the other vessels: pH profile, $CO_2$ profile, dissolved oxygen profile, nutrients profile, temperature profile and stirring speed.

The effect of the variations is assessed by monitoring the cell culture solution 407, during and after the experiment run, to determine one or more of: cell count, cell viability, cell size, biomass, metabolites and biological molecules, such as the product titre, which may be a protein or antibody. In this way, the effects of the variations in the parameters at the different stages of the run may be evaluated. This is achieved by the aspiration and dispensing of samples to well plates or to a sample cup by the liquid handling station head 302 for analysis as discussed above.

The best set of parameters may then be used as a reference point for further experiment runs.

Alternative Embodiments

Rather than being mounted to the cell culture module base 202, the drive mechanism 226 may be mounted directly to the clamp plate 240. That way, the drive mechanism is removable with the clamp plate.

Moreover, rather than having a single drive input motion for each cell culture module 200 converted into multiple rotary drive output motions, each drive element 254 may be directly driven via a respective drive mechanism, such as a motor mounted to the clamp plate 240. In this manner, each stirrer 416 may be driven independently. Intermediate embodiments are also conceivable, with multiple groups of drive elements 254 being driven by respective drive mechanisms 226 and associated drive couplings 230, all mounted to the clamp plate 240.

Alternatively, in another embodiment, the drive connection between the drive mechanism 226 and the stirrers 416 of the individual vessels 400 is established directly, without the intermediary of the clamp plate 240. In this embodiment, the shafts 250 are omitted from the smaller holes 248 in the clamp plate 240 and the drive pins 234 of the drive coupling 230 are received in an off-axis hole in the top of the stirrer shafts 420, replacing the drive input 424. Of course, alternative drive connections could also be envisaged. The stirrer shafts 420 may be longer than those of the preceding embodiments and be received in the respective smaller holes 248 in the clamp plate 240. Alternatively, the clamp plate 240 could be omitted altogether in this embodiment.

Instead of each of $O_2$, $N_2$ and $CO_2$ being supplied via the valve assembly 210, just a selected two of those gases could be supplied. For example, just $O_2$ and $N_2$ can be supplied. As discussed above, the $CO_2$ is provided to maintain the pH levels within a predetermined profile. However, that could be achieved in other ways, such as by dispensing, e.g., bicarbonate of soda or ammonia into the vessel contents. Accordingly, with such alternate pH level control, the $CO_2$ supply could be omitted. Where just two gases are supplied, the valve assembly of course only requires two banks of valves.

Instead of a mixture of $O_2$ and $N_2$ being used to control the dissolved oxygen concentration in the cell culture solution 407, a combination of $O_2$ and air, or a combination of air and $N_2$ could be used. Also the $O_2$ gas could be provided for example as 50% $O_2$ and then mixed with either air or $N_2$.

In fact, it is conceivable that just a single gas or even no gas at all could be supplied. For example, it is known to rely on the diffusion of ambient air to supply $O_2$ and $N_2$ to the system. However, such a system would not be representative of a full-scale process, because such full-scale processes almost invariably have at least one gas supply.

More than three gases could be supplied, in which case an additional bank of valves 213 and associated output conduits 218 for each additional gas would be needed.

The fluid connection between vessel inlet port 412 and the clamp plate 240 (via the clamp plate outlet ports 256 and their connection to the base outlet ports 222 via the clamp plate inlet ports 260) has been described in terms of a gas input connection.

It will be appreciated that the input(s) could instead be in liquid form. Moreover, it will be appreciated that the fluid path could be reversed, with the port in the vessel being an outlet port, and fluid being extracted from the vessel via the fluid connection. That extraction could be for monitoring the contents of the vessel, be that the gases in the headspace 409 or the cell culture solution 407, the fluid connection taking the extracted samples for analysis. Such monitoring via the cell culture module 200 may replace the methods described above for aspirating samples via the fluid transfer port 406 for analysis.

The vessels 400 have been described as having a single inlet port 412, but it will be readily understood that more ports could be provided, with appropriate modifications being made to the associated fluid connections in the clamp plate 240 and the remainder of the cell culture module 200.

The drive connection between the drive mechanism and the respective stirrers has been described in terms of a mechanical connection between a drive pin and an associated driven hole. It will be understood that the mechanical elements could be reversed, with the drive coupling having an array of holes in which are received respective eccentrically disposed driven pins on the respective stirrers.

Instead of a parallelogram linkage to convert the rotary motion of a motor into an eccentric motion, the person skilled in the art will readily conceive of alternative methods of converting input rotary motion into output eccentric motion, or output rotary motion.

It is also possible to transmit the drive non-mechanically, such as by electromagnetic forces. For example, as a simple substitution, the driven element may comprise a magnet or a ferromagnetic element and the drive element may comprise a respective complementary ferromagnetic element or magnet, drive motion being conveyed via ferromagnetic forces between the respective magnet and ferromagnetic element. Alternatively, rather than an eccentric drive mechanism, a simple rotating motion of a drive magnetic element could be transmitted to a rotation of a driven magnetic stirring element, which would not have to include a shaft.

A heater could be supplied for each vessel 400, in which case the temperature within individual vessels could be controlled via associated feedback control. Thus, the temperature profiles of different vessels could be varied relative to one another.

In order to prevent condensation in the upper portions of the vessels 400, heaters may be located near those upper portions, for example within the clamp plate 240 or in the region of the upper surface 224 of the cell culture module base 202.

As described, the sparge tube 410 extends to the bottom of the vessel 400 to supply gases directly into the cell culture solution 407. It will be understood, however, that the sparge tube could be shorter, just extending into the headspace 409 to supply gases into the headspace, which gases would then diffuse into the cell culture solution 407. In fact, the sparge tube could be omitted entirely, with gases being supplied directly into the headspace via the port 412.

Rather than or as well as the pH and DO sensor spots 426, 428 and associated detectors 126a, 126b, alternative sensors could be used. Examples include sensors for detecting: the $CO_2$ concentration, the temperature, cell count, cell viability, cell size, biomass, metabolites and biological molecules.

Also, rather than being detected remotely, for example by fluorescent effects, the parameters could be detected more directly by a probe inserted into the cell culture solution 407 and/or into the headspace 409. Such a probe could be integral with the vessel 400 or could be attached to the clamp plate 240.

Another alternative sensing means could comprise an IC chip located within the vessel 400 and having contacts either within the vessel for connecting with an interrogating probe or accessible through a wall, to transmit signals directly from the chip.

The liquid handling station head 302 is described in terms of a single pipette handler, but it will readily be understood that an array of such handlers could be provided, each under individual control, so as to handle multiple liquid handling operations at the same time.

The invention claimed is:

1. A bioreactor system, including a cell culture module comprising:
   a. a base including a receiving station for removably receiving a plurality of bioreactor vessels at respective locations;
   b. a drive mechanism; and
   c. a clamp plate, removably connectable to the base and connectable to the drive mechanism, for transmitting input motion from the drive mechanism into multiple rotary motion outputs, each output corresponding to a respective vessel location in the receiving station;
   wherein the drive mechanism is an eccentric drive mechanism that includes an array of fixed drive elements, and wherein the clamp plate includes a complementary array of rotatable members, each having an off-axis driven element.

2. The system of claim 1, wherein the drive mechanism is adapted to convert a single input motion into the multiple rotary output motions.

3. The system of claim 1, wherein the drive mechanism is integrally connected with the clamp plate.

4. The system of claim 1, wherein the system includes a plurality of reactor vessels.

5. The system of claim 4, wherein the plurality of vessels are formed as a cassette.

6. The system of claim 1, further comprising multiple fluid conduits, and wherein the clamp plate further comprises fluid connectors for forming a fluid connection between the fluid conduits and associated outlet ports in the clamp plate, each outlet port corresponding to a respective vessel location in the receiving station.

7. The system of claim 1, further comprising a valve assembly having multiple fluid supplies, the valve assembly operable to supply a selected fluid to a selected fluid conduit.

8. The system of claim 1, further comprising at least one sensor for determining characteristics of the contents of a vessel.

9. The system of claim 8, wherein the at least one sensor is for detecting one of: the dissolved oxygen concentration, the $CO_2$ concentration, the pH, the temperature, cell count, cell viability, cell size, biomass, metabolites, biological molecules and particle distribution.

10. The system of claim 8, wherein the at least one sensor comprises a light source and a light detector, to determine the characteristics through interrogation of a sensor spot on a vessel.

11. The system of claim 8, wherein the at least one sensor is mounted so as to be movable to a position adjacent to different respective vessel locations.

12. The system of claim 1, further comprising a bed station, on which the cell culture module is mounted or on which multiple cell culture modules are mounted.

13. The system of claim 12, further comprising a liquid handling station, comprising a liquid handling robot capable of addressing each vessel location and dispensing and/or aspirating fluids to and from vessels at those locations.

14. The system of claim 13, further comprising at least one bioreactor vessel, wherein the liquid handling robot is capable of opening a fluid port in the vessel.

15. The system of claim 6, further comprising at least one bioreactor vessel having at least one fluid port, wherein the at least one vessel is received in the receiving station and wherein a fluid connection is established between the at least one fluid port in the vessel and a respective one of the multiple outlet ports in the clamp plate.

16. The system of claim 6, further comprising a valve assembly having multiple fluid supplies, the valve assembly operable to supply a selected fluid to a selected fluid conduit.

17. A bioreactor system, including a cell culture module comprising:
   a. a base including a receiving station for removably receiving a plurality of bioreactor vessels at respective locations;
   b. a drive mechanism;

c. a clamp plate, removably connectable to the base and connectable to the drive mechanism, for transmitting input motion from the drive mechanism into multiple rotary motion outputs, each output corresponding to a respective vessel location in the receiving station; and d. at least one bioreactor vessel having a stirrer, wherein the at least one vessel is received in the receiving station and wherein a drive connection is established between a respective one of the multiple rotary motion outputs and the stirrer;

wherein the drive mechanism is an eccentric drive mechanism that includes an array of fixed drive elements, and wherein the clamp plate includes a complementary array of rotatable members, each having an off-axis driven element.

18. The system of claim 17, wherein the system includes a plurality of reactor vessels.

19. The system of claim 18, wherein the plurality of vessels are formed as a cassette.

20. A bioreactor system, including a cell culture module comprising:

a. a base including a receiving station for removably receiving a plurality of bioreactor vessels at respective locations;

b. at least one bioreactor vessel having a stirrer, wherein the at least one vessel is received in the receiving station; and c. a drive mechanism comprising at least a portion that is removably connectable to the base for transmitting input motion into multiple rotary motion outputs, each output corresponding to a respective vessel location in the receiving station, wherein a drive connection is established between a respective one of the multiple rotary motion outputs and the stirrer;

d. multiple fluid conduits; and a clamp plate, removably connectable to the base, and including fluid connectors for forming a fluid connection between the fluid conduits and associated multiple outlet ports in the clamp plate, each outlet port corresponding to a respective vessel location in the receiving station;

wherein the drive mechanism is an eccentric drive mechanism that includes an array of fixed drive elements, and wherein the clamp plate includes a complementary array of rotatable members, each having an off-axis driven element.

21. A bioreactor system, including a cell culture module comprising:

a. a base including a receiving station for removably receiving a plurality of bioreactor vessels at respective locations;

b. at least one bioreactor vessel having a stirrer, wherein the at least one vessel is received in the receiving station; and c. a drive mechanism comprising at least a portion that is removably connectable to the base for transmitting input motion into multiple rotary motion outputs, each output corresponding to a respective vessel location in the receiving station, wherein a drive connection is established between a respective one of the multiple rotary motion outputs and the stirrer;

wherein the drive mechanism is an eccentric drive mechanism that includes an array of fixed drive elements, and wherein at least one of the vessels comprises an off-axis driven element in the top of the stirrer.

22. The system of claim 21, further comprising:

a. multiple fluid conduits; and b. a clamp plate, removably connectable to the base, and including fluid connectors for forming a fluid connection between the fluid conduits and associated multiple outlet ports in the clamp plate, each outlet port corresponding to a respective vessel location in the receiving station.

23. The system of claim 22, further comprising a valve assembly having multiple fluid supplies, the valve assembly operable to supply a selected fluid to a selected fluid conduit.

24. The system of claim 22, further comprising at least one sensor for determining characteristics of the contents of a vessel.

25. The system of claim 24, wherein the at least one sensor is for detecting one of: the dissolved oxygen concentration, the $CO_2$ concentration, the pH, the temperature, cell count, cell viability, cell size, biomass, metabolites, biological molecules and particle distribution.

26. The system of claim 24, wherein the at least one sensor comprises a light source and a light detector, to determine the characteristics through interrogation of a sensor spot on a vessel.

27. The system of claim 24, wherein the at least one sensor is mounted so as to be movable to a position adjacent to different respective vessel locations.

28. The system of claim 22, further comprising at least one bioreactor vessel having at least one fluid port, wherein the at least one vessel is received in the receiving station and wherein a fluid connection is established between the at least one fluid port in the vessel and a respective one of the multiple outlet ports in the clamp plate.

29. The system of claim 22, wherein the system includes a plurality of reactor vessels.

30. The system of claim 29, wherein the plurality of vessels are formed as a cassette.

* * * * *